(12) United States Patent
De La Torre-Bueno et al.

(10) Patent No.: US 7,801,390 B2
(45) Date of Patent: *Sep. 21, 2010

(54) APPARATUS AND METHOD FOR LABELING ROWS AND COLUMNS IN AN IRREGULAR ARRAY

(75) Inventors: Jose De La Torre-Bueno, Encinitas, CA (US); Peter Salamon, San Diego, CA (US)

(73) Assignee: Carl Zeiss MicroImaging GmbH, Jena (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/277,147

(22) Filed: Nov. 24, 2008

(65) Prior Publication Data

US 2009/0169077 A1 Jul. 2, 2009

Related U.S. Application Data

(63) Continuation of application No. 11/634,747, filed on Dec. 5, 2006, now Pat. No. 7,457,481, which is a continuation of application No. 10/094,900, filed on Mar. 8, 2002, now Pat. No. 7,146,062.

(60) Provisional application No. 60/274,688, filed on Mar. 8, 2001.

(51) Int. Cl.
  *G06K 9/36* (2006.01)
(52) U.S. Cl. .................. 382/288; 382/129; 382/224; 382/289; 702/152
(58) Field of Classification Search ................. 382/129, 382/224, 225, 288, 289, 291; 702/152; 422/68.1; 436/518

See application file for complete search history.

(56) References Cited

U.S. PATENT DOCUMENTS

| | | | |
|---|---|---|---|
| 6,618,494 B1 * | 9/2003 | Nonay et al. ................. 382/132 |
| 2003/0039384 A1 * | 2/2003 | Bacus et al. ................. 382/128 |
| 2006/0007345 A1 * | 1/2006 | Olson et al. .................. 348/345 |
| 2006/0204072 A1 * | 9/2006 | Wetzel et al. ................ 382/133 |

* cited by examiner

*Primary Examiner*—Samir A. Ahmed
*Assistant Examiner*—Ali Bayat
(74) *Attorney, Agent, or Firm*—Patterson Thuente Christensen Pedersen, P.A.

(57) ABSTRACT

The apparatus and method of the invention provide for assigning coordinates to samples in an array. The method is based on a hierarchical pattern matching to a local lattice structure that is used as a template. Starting from the best local match, the pattern is expanded hierarchically to encompass the entire array.

20 Claims, 12 Drawing Sheets

Conservative

Liberal

Conservative

Liberal

Conservative

Liberal

Conservative

Liberal

*Conservative*

*Conservative*

*Liberal*

*Liberal*

*Mixed*

*Mixed*

*Conservative*

*Conservative*

*Liberal*

*Liberal*

*Mixed*

*Mixed*

Conservative

Conservative

Liberal

Liberal

Mixed

Mixed

APPARATUS AND METHOD FOR LABELING ROWS AND COLUMNS IN AN IRREGULAR ARRAY

CROSS REFERENCE TO RELATED APPLICATIONS

This application is a continuation of application Ser. No. 11/634,747, filed Dec. 5, 2006 now U.S. Pat. No. 7,457,481, which is a continuation of application Ser. No. 10/094,900, filed Mar. 8, 2002, now U.S. Pat. No. 7,146,062 issued Dec. 5, 2006, which claims the benefit of U.S. Provisional Application No. 60/274,688, filed Mar. 8, 2001, each of which are hereby fully incorporated herein by reference.

FIELD

The disclosure relates generally to light microscopy and, more particularly, to automated light microscopic methods and an apparatus for detection of objects in a sample.

BACKGROUND

An array is an ordered arrangement of any kind of subject matter. In the biological sciences, an array is generally a two-dimensional arrangement of samples placed upon a support structure. Samples can include, but are not limited to, nucleic acids, proteins, molecules, cells, tissues and any combination thereof. These arrays allow for the efficient and rapid processing of large numbers of samples, allowing laboratories to process thousands of samples a day. For example, a microplate configured with a four by four matrix of biosites or samples in each of the 96 wells of a microtiter plate would be able to perform a total of 1536 nearly simultaneous tests utilizing a proximal CCD imager. A microplate configured with a 15 by 15 matrix of samples in each of the 96 wells enables a total of 21,600 nearly simultaneous reactions to be processed.

Arrays of samples are used in many forms and for many areas of science, including, but not limited to, 96 well plates or slides for combinatorial chemistry, multi-well carriers for synthesizers, and papers, such as nitrocellulose and nylon, for hybridization reactions. Array technology can be used with almost any clinical or research protocol. For example, in screening libraries, the library, consisting of recombinant clones or molecules, can be placed in two-dimensional arrays on supports, examples of supports can include a microtiter plate or microscope slide. Each clone or molecule can be identified by the identity of the plate and the clone or molecule location (row and column) on that plate. The arrayed libraries can then be used for many applications such as screening for a specific gene of interest or for identifying potential lead compounds for treating diseases. Arrays can also be used to diagnosis diseases as well as synthesize nucleic acids, polypeptides, and chemical compounds. As another example, arrays of tissue can be arranged on a microscope slide to simultaneously test an experimental treatment for diseased tissues.

Current designs rely on the wells or dots being in predictable positions so they can be processed or read by robotic equipment. If, for any reason, the positioning is not as expected, a possible response by a computerized system is to shut down processing of the array. Augmenting a vision system with a method for accommodating irregular arrays would allow robotic systems of this type to recover from minor positioning errors.

Examples of arrays are shown in FIGS. 1 and 4. FIGS. 1 and 4 depict slides with samples 2 thereon. In the case where the samples are of tissue sections, tissue samples may be embedded in a block of paraffin. Successive slices of paraffin and tissue may then be mounted on the slide or series of slides. The slides with the samples, tissues in paraffin, can then be subjected to a battery of test.

In identifying and assigning coordinates to the samples, several image irregularities may hinder machine determination of the row and column coordinates of the centroids. Reasons for the irregularities range from human error to shearing of the paraffin during handling. The irregularities make it difficult to know with certainty the correct labeling in the areas of these irregularities.

Even when a guide is employed, the regularity with which the tissue can be placed into the paraffin may be less than perfect. The tissue sections may be subject to deformation during the transfer to the slide, and some samples may fail to adhere to the slide. In cases where samples in liquid are applied to a support of the array, the liquid dispenser may inadvertently omit samples, for example, failure to pick up the liquid sample, or introduce extraneous "samples," for example, the liquid sample may inadvertently drip from the liquid dispenser or stray marks are introduced by mishandling the slide. Moreover, rows and/or columns, or portions thereof, of samples may be intentionally omitted to separate different groups of samples.

The digitization process introduces further noise to challenge the row and column identification. The noise level may be sufficiently high that a simple round to the nearest integer in $$n_{cols} * X/X_{max} \tag{1}$$

does not reveal the centroid's column coordinate, where X is the x coordinate of the "centroid in question, $X_{max}$ is the greatest x coordinate of all the centroids, and $n_{cols}$, is the number of columns on the slide.

FIGS. 1-6 illustrate some problems in identifying the coordinates of the centroids. FIGS. 2 and 3 and FIGS. 5 and 6 are exploded views of exemplary problem regions in FIGS. 1 and 4, respectively. An array of (x,y) pairs represents the position of the centroids of the tissue samples on the slides. FIG. 1 appears to be fairly regular to the eye with well-defined rows and columns, but zooming into the array illustrates problem areas. FIG. 2 illustrates problems due to missing samples and deviation of samples from straight columns. FIG. 3 illustrates two different problems: two samples lay in what seems to be a missing row (third row from the top) and the correspondence between the bottom rows in the left half and the right half of the image is not clear.

The problem of sparse data is evident in various regions of FIG. 4, which are shown in exploded views in FIGS. 5 and 6. In FIGS. 5 and 6, it is difficult to determine the row and column numbers of the samples, especially when using an algorithm based on local structure.

BRIEF SUMMARY

In accordance with the present invention, a method for assigning coordinates to a centroid in an array would include the steps of providing an array to be analyzed; selecting a starting centroid within the array by using a local lattice structure and determining a quality of fitness for each centroid; assigning coordinates to the starting centroid; and diffusing outward to determine and assign coordinates to neighboring centroids using the lattice structure. While the present invention can be used with arrays whose samples are in perfect alignment, the present invention is especially useful when the array is irregular. The present invention can analyze all the centroids of the array or the centroids located on portions of the array.

In some embodiments of the invention, a quality of fitness value is calculated for a given centroid, $(x_c, Y_c)$. The quality of fitness value being determined by the equation $$\text{Fitness}(x_c, y_c) = \underset{v_a, v_b}{\text{Min}} \left( \sum_{k=1}^{N} ((x_k - x_{grid(k)})^2 + (y_k - y_{grid(k)})^2) \right).$$

A local lattice structure can be a grid having a center centroid $(x'' y_c)$. N is the number of neighboring centroids $(x_k, y_k)$ and $v_a$ and $v_b$ are adjusted to minimize the sum of the squared distances from an actual position of each of the neighboring centroids to the nearest lattice point. The lattice points relative to the center centroid can be calculated by the equation $$(x_{grid}, y_{grid}) = (x_c, y_c) + K \cdot v_a + L \cdot v_b$$

wherein K and L are integers and $v_a$ and $v_b$ are two lattice vectors that describe the lattice structure. Each neighboring centroid can be associated with a point of the lattice by minimizing $$(x_k - x_{grid})^2 + (y_k - y_{grid})^2$$

over K and L for any given value of $v_a$ and $v_b$ for the grid as defined by $$(x_{grid}, y_{grid}) = (x_c, y_c) + K \cdot v_a + L \cdot v_b.$$

The grid of the lattice structure can be of any size, limited only in that the grid must accommodate a center centroid and neighboring centroids. Thus, the grid can be a three-by-three grid having eight neighboring lattice points, a five-by-five grid having 24 neighboring lattice points, a seven-by-seven grid having 48 neighboring lattice points, and so on.

In some embodiments, the method includes a step of identifying (labeling) suspicious points (centroids) by determining whether the quality of fitness of a given centroid is greater than a first tolerance level or whether the lattice vectors associated with the centroid relative to the lattice vectors associated with the starting centroid is greater than a second tolerance level.

The step of identifying the suspicious point can be executed before the step of determining the starting centroid or before the step of diffusing outward. Additionally the step of identifying the suspicious point can be done periodically throughout the diffusing step, or after each centroid has been selected as the center centroid and the centroids on the grid have been assigned coordinates.

The first tolerance level, for identifying suspicious points, is $\epsilon_1$ and is defined by $$\epsilon_1 = N(M\delta_1)^2$$

wherein N is a number of neighbors, M is a mean lattice spacing of the best lattice structure as defined by $$M = \frac{1}{2}(\|v_a^*\| + \|v_b^*\|)$$

and $\delta_1$ represents the average deviation between a lattice point and a neighboring centroid in units of M.

The second tolerance level is defined by $$\epsilon_2 > \left| \frac{\|v_i\|}{\|v_i^*\|} - 1 \right|; i = a, b$$

wherein $\epsilon_2 = \delta_2$ and $\delta^2$ is a user specified tolerance threshold.

In some embodiments, the step of diffusing outward includes selecting one of the neighboring centroid $(x_k, y_k)$ as a new center centroid. To be a new center centroid, the centroid must not have been identified (labeled) as suspicious or ambiguous, or previously been a center centroid. The method also includes the steps of assigning the new center centroid a relative coordinate $(I_k, J_k)$; providing a lattice structure comprising a grid; locating a neighboring centroid to the new center centroid closest to a point on the grid of the lattice structure using an equation $$(x_{grid}, y_{grid}) = (x_k, y_k) + K v_a^k + L v_b^k;$$

and assigning the neighboring centroid a relevant coordinate using the equation $$(I_{new}, J_{new}) = (I_k, J_k) + (K, L).$$

The neighboring centroid, however, may not be assigned relative coordinates if the distance as defined by $\sqrt{(x - x_{grid})^2 + (y - y_{grid})^2}$ is greater than a third tolerance level defined as $\epsilon_3$. The third user specified tolerance level $\delta_3$ is defined by $$\delta_3 = \epsilon_3 / M.$$

In some embodiments, the grid of the lattice structure used in the diffusing step is of a different size than the grid used for determining a starting centroid. In other embodiments, they are the same.

In some embodiments, where the neighboring centroid has already been assigned coordinates, if the previously assigned coordinates do not match the new coordinates, then the centroid will be identified as ambiguous.

In some embodiments, the diffusion steps are repeated until all the centroids in the array, not labeled suspicious or ambiguous, have been the center centroid.

In some embodiments the relative coordinates of the centroids in the array are translated to absolute coordinates. The absolute coordinates can be calculated from the equation $(O,P) = (I,J) - (I_{min}, J_{min}) + (1,1)$ wherein $I_{min}$ and $J_{min}$ represent the smallest assigned I and J values.

In some embodiments, the method further includes the step of outputting data. The data includes the centroids being labeled either with coordinates, identified as suspicious or ambiguous, or remain unlabeled.

In some embodiments, the method for assigning coordinates to centroids in an array is used in an automated system. The method would include the steps of scanning the array; and inputting the scanned image to a receiver for processing the array according to the methods of the invention.

In some embodiments, an array of biological samples is placed in an array carrier. The array carriers are loaded into an input hopper of an automated system. The operator may then enter data identifying the size, shape and location of a scan area on each array, or, preferably, the system automatically locates a scan area for each array during array processing. An operator can then activate the system for slide processing. Alternatively, the processing parameters of the array may be identified by a bar code present on the array or array carrier. Arrays can be made from slides, microtitre plates, multi-well trays, and paper, for example, nitrocellulose or nylon. Other material used in the production of arrays are well known in the art. For example, methods of preparing an array can be found in U.S. Pat. No. 6,312,960, U.S. Pat. No. 6,203,758, U.S. Pat. No. 6,103,479, and U.S. Pat. No. 5,770,151, all of which are incorporated by reference in their entirety.

At system activation, an array carrier can be positioned on an X-Y stage, the entire array is then rapidly scanned, thereby acquiring an image for processing and detecting objects of interest, samples and their centroids. Color, size, density, shape, and texture of the samples can be used to identify these objects of interest. The location of each candidate object of interest can then be stored for further processing, such as assigning coordinates to the objects of interest.

Embodiments of an apparatus of the invention can include a computer program, stored on a computer-readable medium, for assigning coordinates to a centroid on an array, the computer program comprising instructions for causing a computer system to provide an image of an array; select a starting centroid within the array by using a lattice structure and determine a quality of fitness for each centroid; assign coordinates to the starting centroid; and diffuse outward to determine and assign coordinates to a neighboring centroid using the lattice structure. It is contemplated that the method of assigning coordinates can be performed by an algorithm.

Also contemplated is an apparatus, for assigning coordinates to samples (objects of interest) in an array, including a computer having at least one system processor with image processing capability, a computer monitor, an input device, a power supply, and an optical sensing device for acquiring images. The apparatus can also include input and output mechanisms for multiple array analysis and storage.

BRIEF DESCRIPTION OF THE DRAWINGS

FIGS. 1A-11D are schematic drawings of one visualization of the results from the practice of one embodiment of the method of the invention for the array shown in FIG. 1.

DETAILED DESCRIPTION OF THE DRAWINGS

As used herein and in the appended claims, the singular forms "a," "an," and "the" include plural references unless the context clearly dictates otherwise. Thus, for example, reference to "an array" can include a plurality of arrays and a reference to "the centroid" can include reference to one or more centroids, and so forth.

Unless defined otherwise, all technical and scientific terms used herein have the same meaning as commonly understood to one of ordinary skill in the art to which this invention belongs. Although any method, device and material similar or equivalent to those described herein can be used in the practice of the invention, the preferred methods, devices and materials are now described.

The apparatus and method described herein, for assigning coordinates to samples of an array, work from an initial list of centroids. A centroid represents the center of mass of a sample or a putative sample; therefore, in the analysis, a centroid corresponds to a sample of the array. In practicing the invention, the apparatus and method associate to each centroid a set of coordinates, for example, a row and a column in the array, or identify the centroid as a suspicious or ambiguous point that should be excluded from the regular array.

The inventive apparatus and method for labeling rows and columns in arrays of samples can accommodate the irregularities of the array described above. The apparatus and method proceed via a sequence of deductions concerning the lattice structure of the array. The apparatus and method begin from a region that conforms well to a local lattice structure and spreads out from this initial seed.

Figure 7:
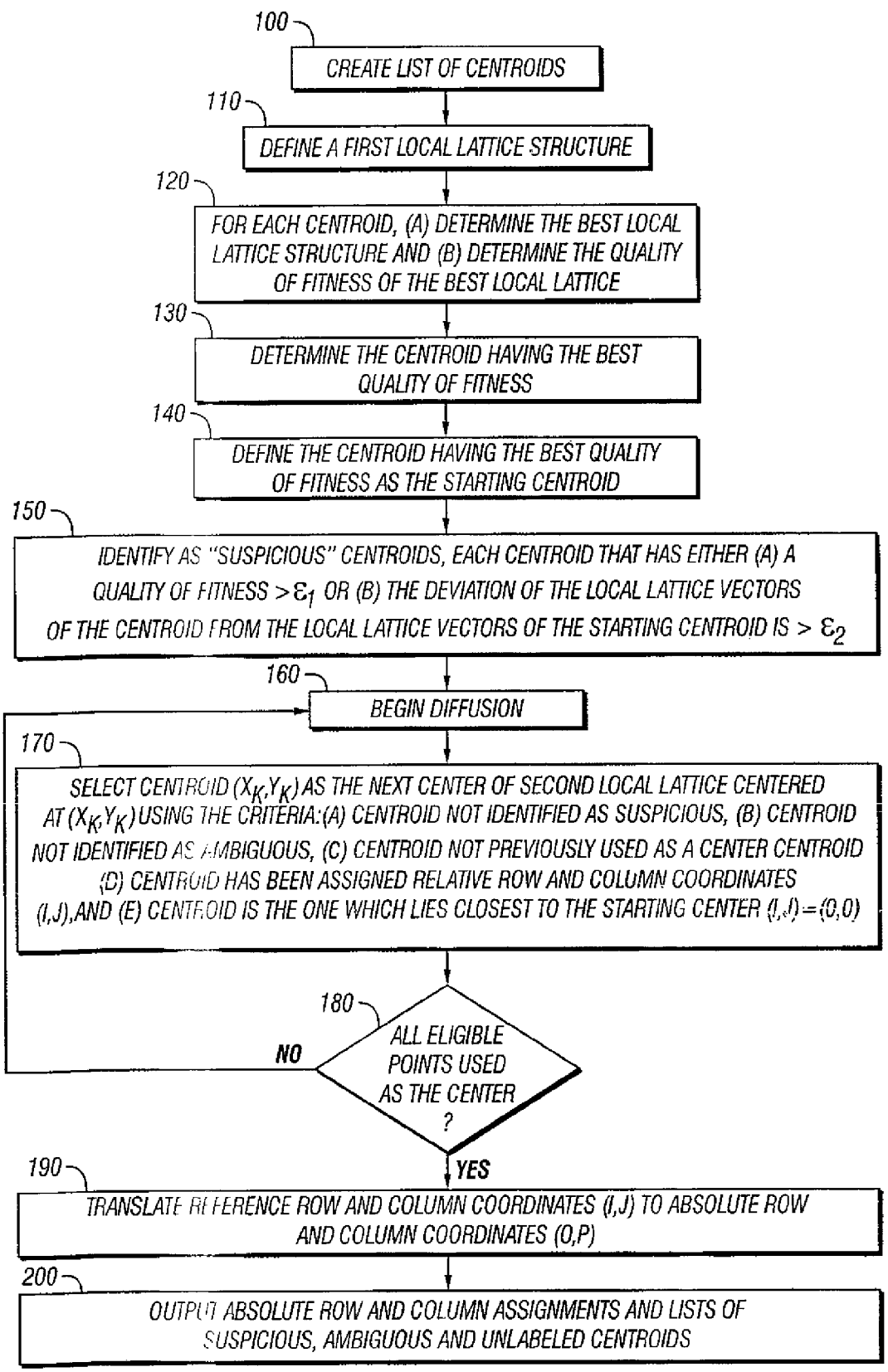
FIG. 7 is a flow chart describing one embodiment of the method of the present invention.

FIG. 7 illustrates one embodiment of the method for labeling rows and columns in an array of samples. A list of centroids is created from an array of samples 100. The method searches for a starting region, defined as a region of centroids that best matches a local lattice structure 110. The local lattice may be, for example, a three-by-three grid of points representing a center centroid and its eight nearest neighboring centroids. The size of the grid of the local lattice structure may be of any size and is only limited in that it have a center point, thus another example is a five-by-five grid.

The method selects a best local lattice structure for the centroids and calculates a measure of the quality of fitness of the lattice to the centroids 130. The calculated values are then sorted by their quality of fitness to determine the centroid having the best quality of fitness value and defining that centroid as the starting point 140.

The measure of the quality of fitness of a lattice structure for a given centroid is computed as follows. The lattice points relative to a center centroid $(x_c, y_c)$ are given by the equation $$(x_{grid}, y_{grid}) = (x_c, y_c) + K \cdot v_a + L \cdot v_b \qquad (2)$$

where K and L are integers and $v_a$ and $v_b$ are the two lattice vectors that describe the local lattice and that remain to be determined as part of the fit. In the case of a local lattice having an three-by three grid, the eight closest centroids $N8 = \{(x_k, y_k), k=1, \ldots, 8\}$, are each associated with a node, or point, on the model grid by minimizing the equation $$(x_k - x_{grid})^2 + (y_k - y_{grid})^2 \qquad (3)$$

over the values of K and L for any given values of $v_a$ and $v_b$ where $(x_{grid}, y_{grid})$ are as defined in equation (2). The grid parameters $v_a$ and $v_b$ are then adjusted to minimize the sum of the squared distances from the actual positions of the eight centroids closest to $(x_c, y_c)$ and their nearest lattice points. Specifically, the quality of fitness, $\text{Fit}(x_c, y_c)$, for a given centroid, $(x_c, y_c)$ is determined by the equation $$\text{Fit}(x_c, y_c) = \underset{v_a, v_b}{\text{Min}}\left(\sum_{k=1}^{N}((x_k - x_{grid(k)})^2 + (y_k - y_{grid(k)})^2)\right) \quad (4)$$

where N is the number of neighboring centroids, in this case eight. The sum of these eight squared distances is the measure of the quality of fitness of a region's local lattice match.

Given reasonably close starting values of $v_a$ and $v_b$, a local optimization can be carried out analytically. The choice of K and L for a given center centroid $(x_c, y_c)$, its neighboring centroids $(x_k, y_k)$, and lattice vectors $v_a$ and $v_b$ is achieved by expressing the displacement $(x_k-x_c, y_k-y_c)$ as a linear combination of $v_a$ and $v_b$, and rounding the coefficients to the nearest integers. Using these integers $K_k$ and $L_k$ for the $(x_{grid(k)}, y_{grid(k)})$ positions, the resulting objective function is quadratic in the four unknowns $v_a=(v_{ax}, v_{ay})$ and $v_b=(v_{bx}, v_{by})$. Setting the four partial derivatives of the objective function in equation (4) equal to zero, gives four linear equations which may be solved for the optimal values of $v_a$ and $v_b$. The solution determines the horizontal and vertical vectors that generate the best model grid for the region. The starting values of $v_a$ and $v_b$ are $v_a=(X_{max}/n_{cols},0)$, and $v_b=(0,Y_{max}/n_{rows})$.

Once a region with the best quality of fitness value is found, its $v_a$ and $v_b$ are used as initial values for the next optimization.

The previous paragraphs describe how each centroid is assigned an associated pair of lattice vectors $v_a$ and $v_b$ and a quality of fitness value. The starting point of the method is the centroid with the best quality of fitness value. This starting centroid is assigned relative row and column coordinates $(1,J)=(0,0)$ and its lattice vectors are denoted by $v_a^*$ and $v_b^*$.

Referring to the embodiment shown in FIG. 7, once the starting centroid is identified, the diffusion step can proceed 160. However, before beginning the step of assigning coordinates to the remaining centroids by way of the outwardly diffusion process, "suspicious points" in the list of centroids are identified 150. Because these suspicious points question whether this centroid is a real sample or merely a mistake, these suspicious points will not be a center centroid during the diffusion process.

Suspicious points can be identified by either (a) having a quality of fitness value as determined by equation 4 above some tolerance level $\epsilon_1$, or (b) having a value when the local lattice vector associated with the centroid in question is compared to the local lattice vectors associated with the starting centroid (which has been determined to have the best quality of fitness value) above some tolerance level $\epsilon_2$. The tolerance levels can be user specified.

In one embodiment, the tolerance levels can specify limiting values of certain quantities calculated from the (x,y) coordinates of the centroids and, as such, may be highly dependent on the scale used in digitizing the image. To eliminate this dependence, the values of these tolerance levels, $\epsilon_1$ and $\epsilon_2$, are calculated from user-specified tolerances $\delta_i$, i=1 and 2 which are measured in units of a lattice spacing.

To rescale from units of a lattice spacing to the units used in the digitized grid, it is convenient to define a parameter M, which represents the mean lattice spacing, as $$M = \frac{1}{2}(\|v_a^*\| + \|v_b^*\|)$$

where $v_a^*$ and $v_b^*$ are the lattice vectors of the starting centroid, having been determined that the centroid had the best quality of fitness value. It is also possible to define M by using the scales of $\Delta x$ and $\Delta y$.

Tolerance level $\epsilon_1$ can be defined as $\epsilon_1 = N(M\delta_1)^2$ where N is the number of neighboring centroids, which would be eight for a three-by-three grid. For a centroid to be identified as suspicious, its quality of fitness is greater than the tolerance level $\epsilon_1$ $\epsilon_1 < \text{Fit}(x_c, y_c)$ and $\text{Fit}(x_c, y_c)$ is a sum of N squared deviations and $\delta_1$ represents the average deviation between a lattice point and a neighboring centroid in units of M. The user can also specify that if the quality of fitness is equal to $\epsilon_1$, the centroid should also be labeled as suspicious.

The second tolerance level, $\epsilon_2$, is used to identify suspicious points on the grounds that their lattice vectors deviate too much from the ideal. In the method, this can be measured by $$\varepsilon_2 > \left|\frac{\|v_i\|}{\|v_i^*\|} - 1\right|; i = a, b.$$

Since $\epsilon_2$, specifies a fractional difference, then $\delta_2 = \epsilon_2$.

This makes $\delta_2$ a fractional threshold comparing the size of the locally optimized lattice of the centroid to the best lattice of the starting centroid. This test condition serves to eliminate harmonics. If a set of points is well described by the lattice vectors $v_a$, $v_b$, then they are also well described by $v_a/2$ and $v_b/2$. These locally optimal solutions are called harmonics. If the optimized lattice is too small, then the lattice vectors correspond to higher harmonics. Similarly, if the lattice is too large it is called lower harmonics.

Once all the centroids have been evaluated in order to identify suspicious centroids, the diffusion step proceeds 160. Alternatively or additionally, the method may provide for re-evaluating the centroids periodically to note any changes in the tolerance values. In other words, as the diffusion step proceeds, a centroid may be a neighboring centroid in several lattice structures. As more information is gathered, the tolerance measurements for a centroid may be re-calculated to see if additional information has changed the tolerance measures below the applicable tolerance threshold levels, $\epsilon_1$ and $\epsilon_2$, to justify removal of the suspicious label. This "re-evaluation" of a suspicious point can be done after the assignment of a coordinate, or before the selection of a new center centroid. It can also be done periodically during the diffusion process.

In the diffusion process 160, the method provides for selecting a centroid $(x_k, y_k)$ to be used as the next center of a new local lattice and then assigning row and column coordinates to all the points lying sufficiently near the lattice point, such as those found in a five-by-five grid having a center at $(x_k, y_k)$ 170. The new center must fulfill four criteria:

(a) it has not been labeled suspicious as described in the previous paragraph;

(b) it has not been labeled ambiguous as described below;

(c) it has not been previously used as a center in the method; and (d) it has been assigned relative row and column coordinates (I,J).

Figure 8A:
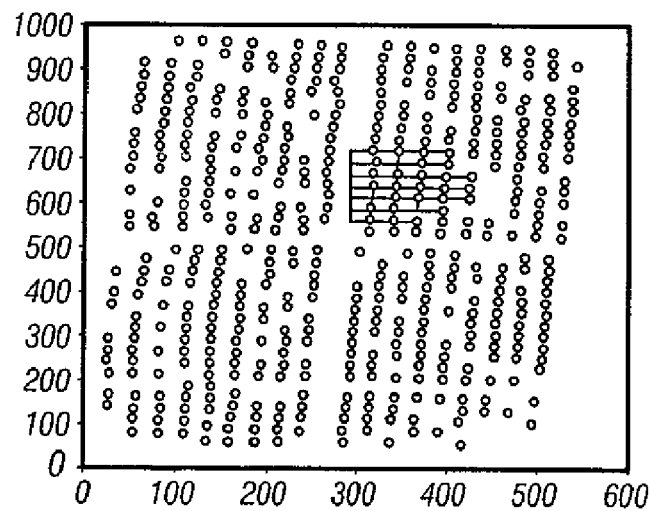
FIGS. 8A-8C are schematic drawings of three time points in the practice of one embodiment of the method of the invention.
Figure 8B:
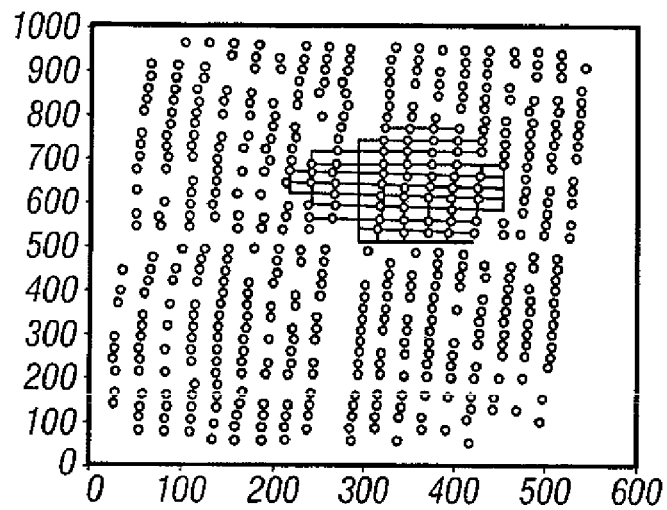
Figure 8C:
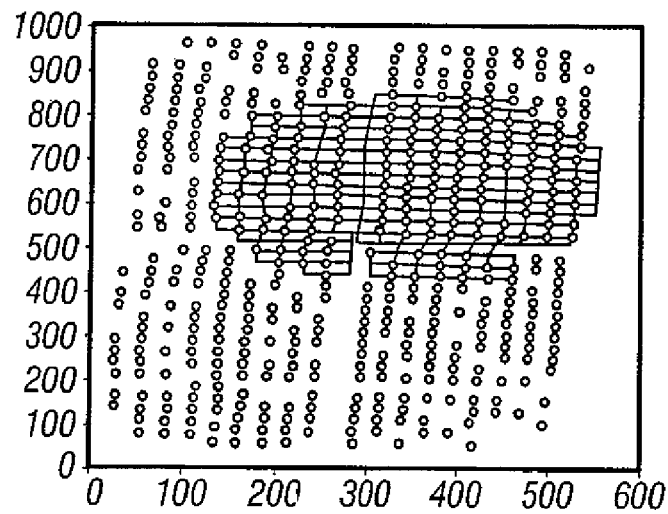

Among the centroids that fulfill these four conditions, the one which lies closest to the starting center (I,J)=(0,0) can be used as the next center centroid. FIGS. 8A-8C depict the diffusion pattern the method of the invention generates as it looks for neighbors to label. Note that condition (d) implies that initially only the starting point can be chosen as a center. The coordinates of the next center centroid is denoted by $(x_k, y_k)$ and its assigned relative row and column coordinates by $(I_k, J_k)$. The diffusion step proceeds to generate the lattice points in the lattice structure. For example, in a lattice structure having a five-by-five grid, 25 lattice points are generated; for each K and L value between −2 and 2, the centroid (x,y) closest to the lattice point is calculated by $$(x_{grid}, y_{grid}) = (x_k, y_k) + K v_a^k + L v_b^k$$

and tentatively assigned the coordinates $$(I_{new}, J_{new}) = (I_k, J_k) + (K, L).$$

These tentatively assigned coordinates are actually assigned to this centroid only if no previous coordinates have been assigned to this point and the distance $$\sqrt{(x - x_{grid})^2 + (y - y_{grid})^2}$$

is less than a third tolerance level $\epsilon_3$. If coordinates have previously been assigned and they do not match the newly calculated coordinates, then the centroid is identified as "ambiguous" and, thus, will not be used as a center.

A user specified tolerance level $\epsilon_3$ is used in the equation $$\epsilon_3 > \sqrt{(x - x_{grid})^2 + (y - y_{grid})^2}$$

to decide whether the neighboring centroid (x,y) of a center centroid should be labeled based on its proximity to the nearest grid point emanating from the center centroid. Therefore, if the third tolerance value of the neighboring centroid is less than $\epsilon_3$ and no previous coordinates have been assigned it, it will be assigned a coordinate. Defining $\delta_3$ by $$\delta_3 = \epsilon_3 / M$$

makes $\delta_3$ scale independent.

The diffusion process continues until all eligible centroids have been used as the center centroid 180. The relative row and column coordinates (I,J) can then be translated to absolute row and column coordinates by the following equation $$(O, P) = (I, J) - (I_{min}, J_{min}) + (1, 1)$$

where $I_{min}$ and $J_{min}$ represent the smallest assigned I and J values 190. Besides the row and column assignments, the output of the present method can include lists of suspicious, ambiguous, and unlabeled centroids 200.

The various techniques, methods, and aspects of the invention described above can be implemented in part or in whole using computer-based systems and methods. Additionally, computer-based systems and methods can be used to augment or enhance the functionality described above, increase the speed at which the functions can be performed, and provide additional features and aspects as a part of or in addition to those of the invention described elsewhere in this document.

Various computer-based systems, methods and implementations in accordance with the above-described technology are presented below.

An apparatus of the invention may include the use of the methods of the invention in conjunction with any of the computer-based systems described herein. The computer-based system may include the means for inputting data either manually or automatically. The system can include devices for scanning the array, or otherwise inputting data about the array, digitizing the image, storing data, processing the data according to the methods described herein, outputting data, or anyone of these functions. Any or all of these functions may be automated.

The processor-based system can include a main memory, preferably random access memory (RAM), and can also include a secondary memory. The secondary memory can include, for example, a hard disk drive and/or a removable storage drive, representing a floppy disk drive, a magnetic tape drive, an optical disk drive, etc. The removable storage drive reads from and/or writes to a removable storage medium. Removable storage media represents a floppy disk magnetic tape, optical disk, etc., which is read by and written to by removable storage drive. As will be appreciated, the removable storage media includes a computer usable storage medium having stored therein computer software and/or data.

In alternative embodiments, secondary memory may include other similar means for allowing computer programs or other instructions to be loaded into a computer system. Such means can include, for example, a removable storage unit and an interface. Examples of such can include a program cartridge and cartridge interface (such as the found in video game devices), a movable memory chip (such as an EPROM, or PROM) and associated socket, and other removable storage units and interfaces which allow software and data to be transferred from the removable storage unit to the computer system.

The computer system can also include a communications interface. Communications interfaces allow software and data to be transferred between computer system and external devices. Examples of communications interfaces can include a modem, a network interface (such as, for example, an Ethernet card), a communications port, a PCMCIA slot and card, etc. Software and data transferred via a communications interface are in the form of signals which can be electronic, electromagnetic, optical or other signals capable of being received by a communications interface. These signals are provided to communications interface via a channel capable of carrying signals and can be implemented using a wireless medium, wire or cable, fiber optics or other communications medium. Some examples of a channel can include a phone line, a cellular phone link, an RF link, a network interface, and other communications channels.

In this document, the terms "computer program medium" and "computer usable medium" are used to generally refer to media such as a removable storage device, a disk capable of installation in a disk drive, and signals on a channel. These computer program products are means for providing software or program instructions to a computer system.

Computer programs (also called computer control logic) are stored in main memory and/or secondary memory. Computer programs can also be received via a communications interface. Such computer programs, when executed, enable the computer system to perform the features of the present invention as discussed herein. In particular, the computer programs, when executed, enable the processor to perform the features of the present invention. Accordingly, such computer programs represent controllers of the computer system.

In an embodiment where the elements are implemented using software, the software may be stored in, or transmitted via, a computer program product and loaded into a computer system using a removable storage drive, hard drive or communications interface. The control logic (software), when executed by the processor, causes the processor to perform the functions of the invention as described herein.

In another embodiment, the elements are implemented primarily in hardware using, for example, hardware components such as PALs, application specific integrated circuits (ASICs) or other hardware components. Implementation of a hardware state machine so as to perform the functions described herein will be apparent to person skilled in the relevant art(s). In yet another embodiment, elements are implanted using a combination of both hardware and software.

In another embodiment, the computer-based methods can be accessed or implemented over the World Wide Web by providing access via a Web Page to the methods of the present invention.

Figure 9:
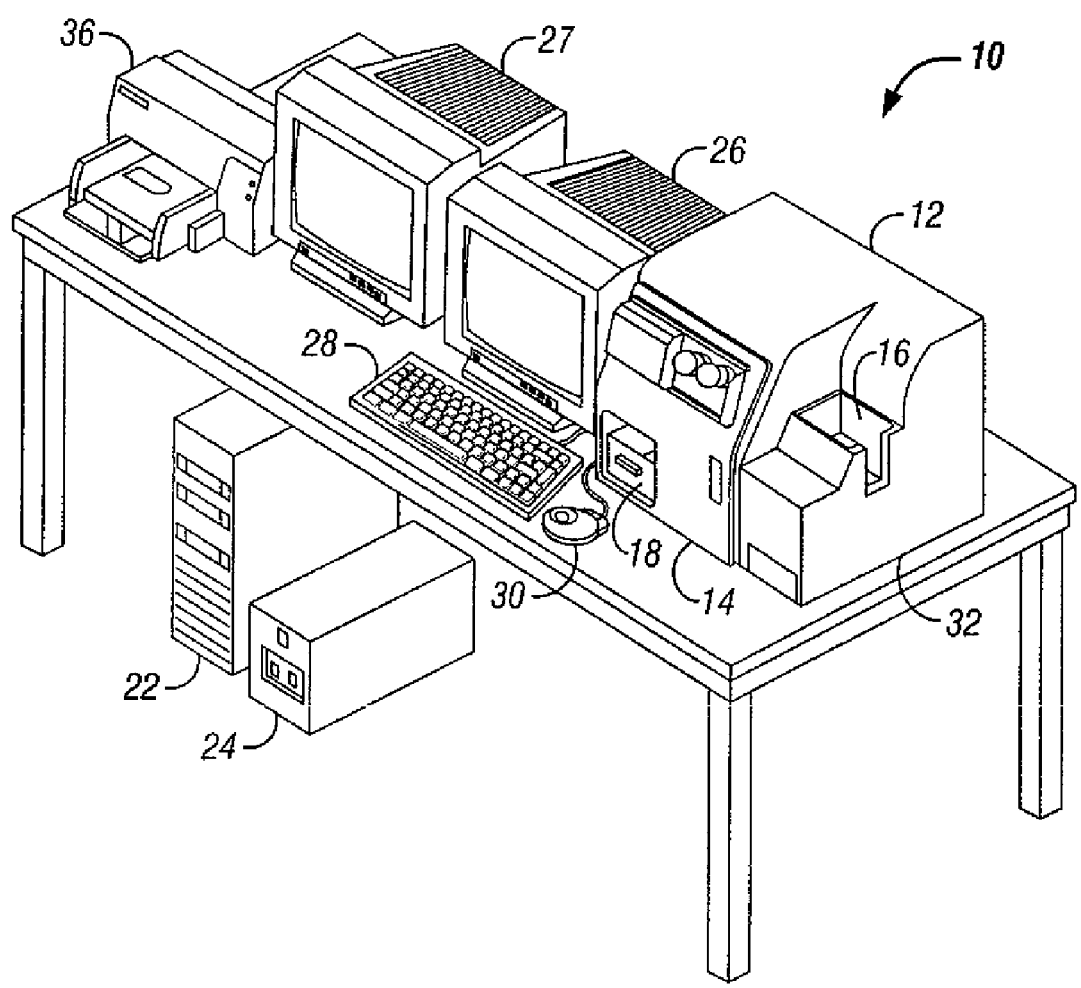
FIG. 9 is a perspective view of one embodiment of an apparatus for automated array analysis according to the present invention.
Figure 10:
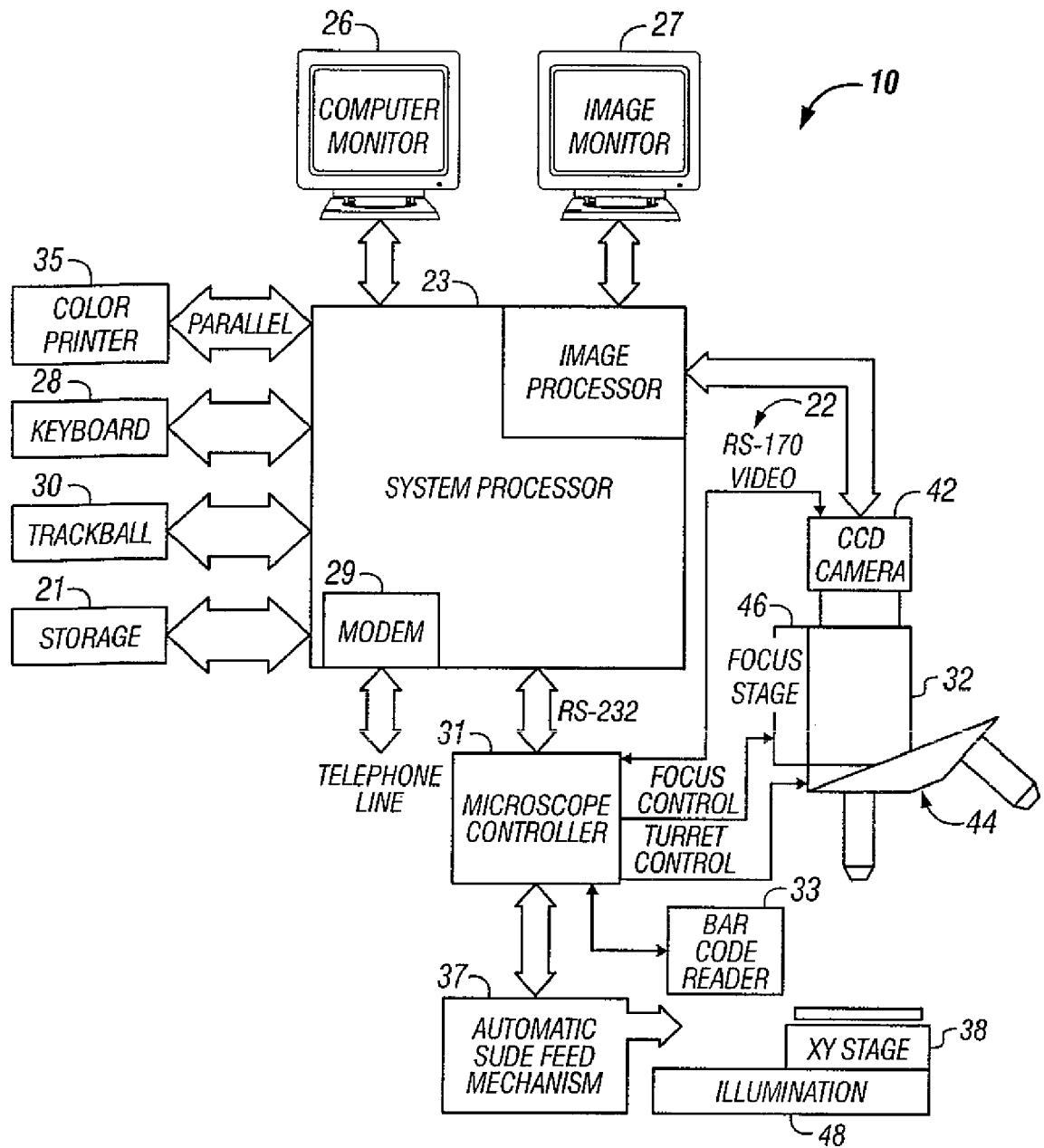
FIG. 10 is a block diagram of the apparatus shown in FIG. 9.

FIGS. 9 and 10 show a perspective view and a block diagram, respectively, of one embodiment of the apparatus of the invention. The apparatus for automatically processing an array is generally indicated by reference numeral 10. The apparatus comprises a scanning subsystem. The scanning subsystem can include a microscope subsystem 32 housed in a housing 12. The housing 12 includes an array carrier input hopper 16 and an array carrier output hopper 18. A door 14 in the housing 12 secures the microscope subsystem from the external environment. A computer subsystem comprises a computer 22 having at least one system processor 23, and a communications modem 29. The computer subsystem further includes a computer monitor 26 and other external peripherals including storage device 21, a pointing device, such as a track ball device 30, a user input device, such as a touch screen, keyboard, or voice recognition unit 28 and color printer 35. The apparatus can also include a separate image monitor 27. An external power supply 24 is also shown for power outage protection. The apparatus 10 further includes an optical sensing device 42, such as a camera, preferably a CCD camera, for acquiring images. Microscope movements are under the control of system processor 23. An automatic array feed mechanism in conjunction with X-Y stage 38 provide automatic slide handling in the apparatus 10. An illumination light source 48 can project light onto the X-Y stage 38 where an array is placed. The array is subsequently imaged through the microscope subsystem 32 and acquired through the optical sensing device 42 for processing by the system processor 23.

In one embodiment, the X-Y stage is moved to scan the image of the array. Alternatively or additionally, it is the microscope subsystem 32 and/or optical sensing device 42 that is moved to scan the array. The apparatus may also include a Z stage or focus stage 46 under control of the system processor 23 to provide displacement of the microscope subsystem in the Z plane for focusing. The microscope subsystem 32 can further include a motorized objective turret 44 for selection of objectives to view the array. In other embodiments, the array is scanned in a manner similar to that of electronic scanners, where an "eye" picks up images and digitalizes it as the "eye" is moved along, directly or indirectly, to the surface of the array.

One purpose of the apparatus 10 is for the unattended automatic scanning of prepared arrays for the detection of samples in the array. The apparatus 10 can then automatically locate and assign coordinates to the samples in the array. A number of stains can be used, if desired, to distinguish the samples from the background. Thus, in one aspect, the samples can be prepared with a reagent to obtain a colored insoluble precipitate. The apparatus of the present invention being used to detect this precipitate as a sample. Other means of distinguishing samples from background include, but are not limited to texture and density analysis. Methods and apparatus of automated image analysis and detection of objects of interest, e.g., samples on slides, are provided in U.S. patent application Ser. No. 09/344,308, filed Jun. 24, 1999; U.S. patent application Ser. No. 09/495,461, filed Feb. 1, 2000; and U.S. patent application Ser. No. 09/616,817, filed Jul. 12, 2002, all of which are explicitly incorporated by reference in their entirety.

During operation of the apparatus 10, a user can mount the prepared arrays onto the input hopper 16. The hopper 16 may utilize an automatic feed mechanism 37. The user can then specify the size, shape and location of the area to be scanned or, alternatively, the system can automatically scan the array. The operator can command the apparatus to begin automated scanning of the array through a graphical user interface. A bar code label can be affixed to the array or array carrier and read by a bar code reader 33 during this loading operation.

The apparatus stores an image of the array for later analysis or review by a user. All results and images can be stored to a storage device 21 such as a removable hard drive, DAT tape, local hard drive, optical disk, or transmitted to a remote site for review or storage. The stored images for each slide can be viewed in a mosaic of images for further review.

The following examples are provided to illustrate the practice of the instant invention and in no way limit the scope of the invention.

Examples

In evaluating the experimental values for δs, Table 1 below shows the range of parameter values that can produce satisfactory performance using a method of the invention. The table also summarizes the meaning and use of each of the parameters.

| Tolerances | Liberal | Conservative | Meaning | Use |
|---|---|---|---|---|
| $\delta_1$ | 0.20 | 0.15 | Mean deviation of neighboring the local lattice | Decide whether to use as center |
| $\delta_2$ | 0.30 | 0.10 | Fractional deviation of local lattice from best lattice vectors | Decide whether to use as center |
| $\delta_3$ | 0.25 | 0.15 | Deviation of one neighbor to point | Decide whether to to neighbor |

Figure 1:
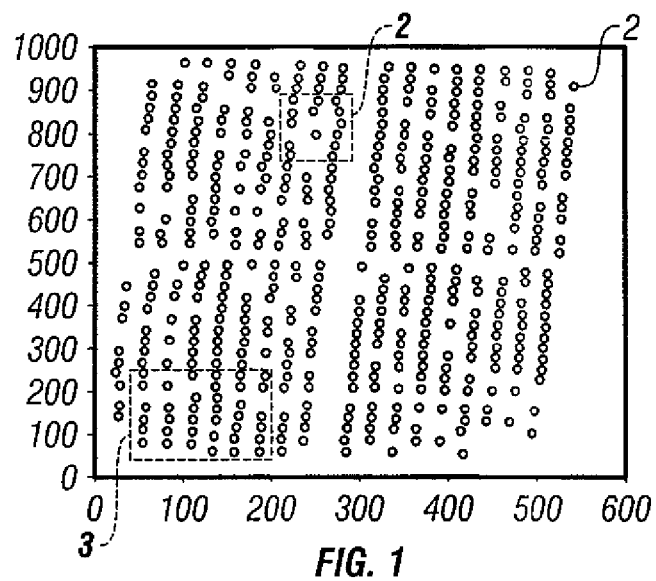
FIG. 1 is a schematic drawing of an exemplary array.
Figure 2:
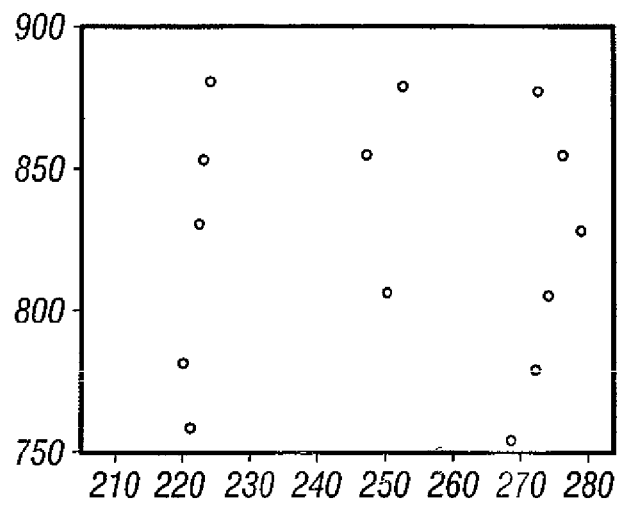
FIG. 2 is an enlarged view of one area of the array shown in FIG. 1.
Figure 3:
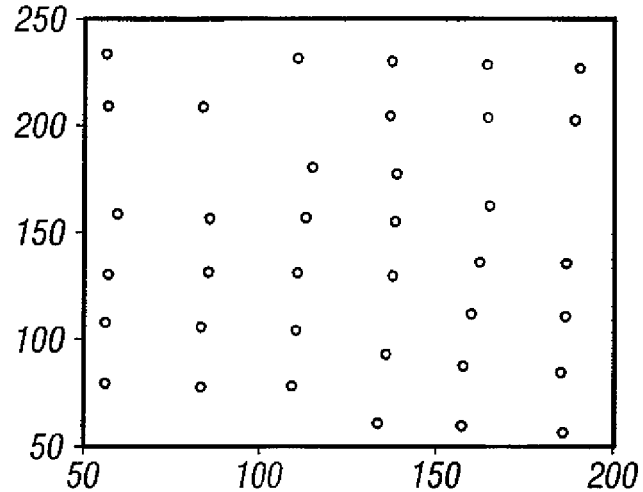
FIG. 3 is an enlarged view of another area of the array shown in FIG. 1.
Figure 4:
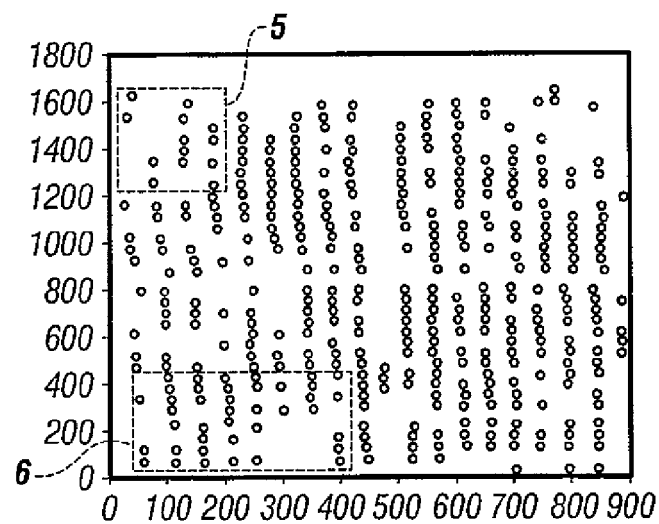
FIG. 4 is a schematic drawing of another exemplary array.
Figure 5:
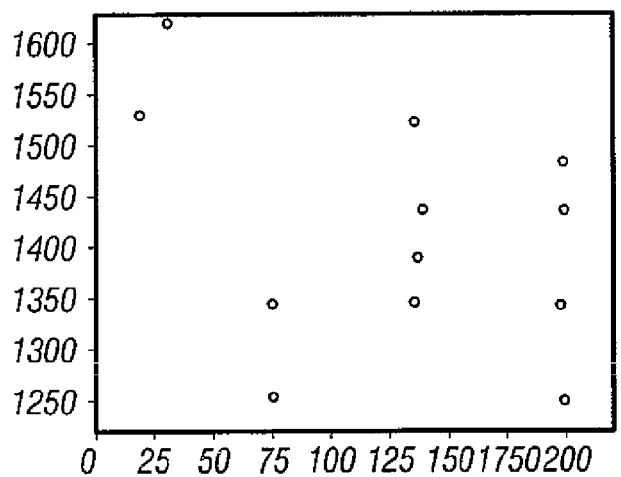
FIG. 5 is an enlarged view of one area of the array shown in FIG. 4.
Figure 6:
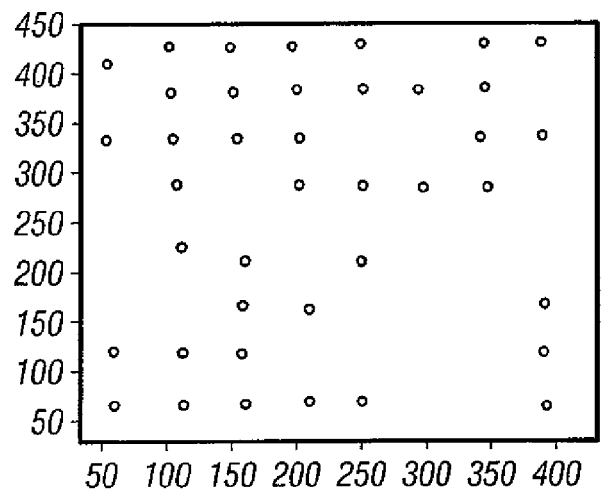
FIG. 6 is an enlarged view of another area of the array shown in FIG. 4.

The method described above performed satisfactorily on all datasets considered. The arrays of FIGS. 1 and 4 show the centroids in the troublesome regions of each figure, i.e., FIGS. 2, 3, 5, and 6, received labels that depended strongly on the parameters used and, therefore, served to define the range of reliable values shown in Table 1.

Figure 11A:
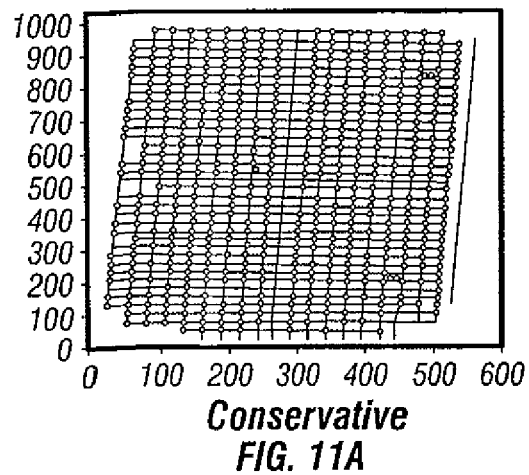
Figure 11B:
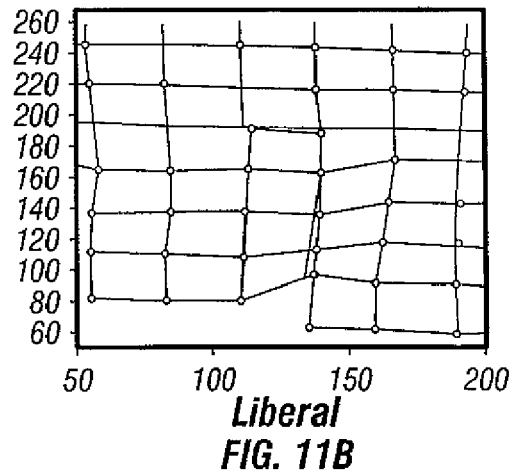
Figure 11C:
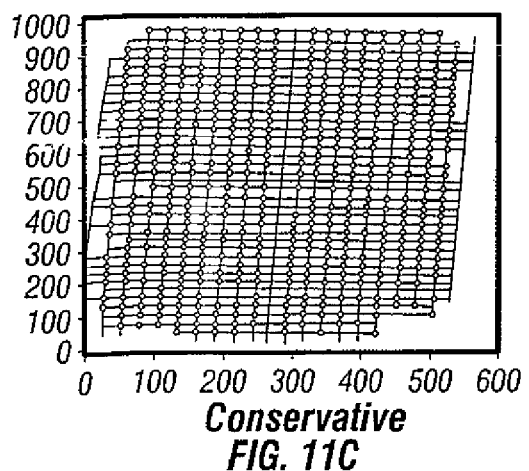
Figure 11D:
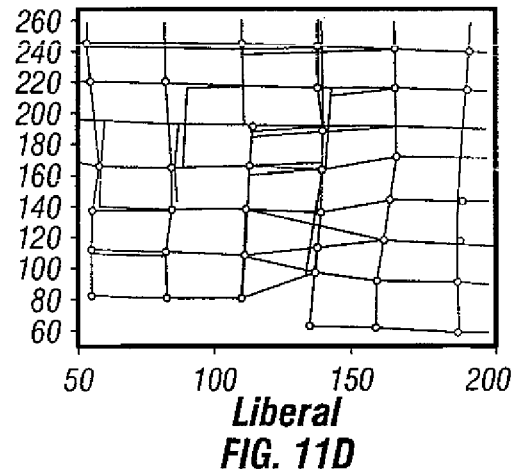

In evaluating the method of the invention, it is useful to introduce three complementary ways of visualizing the results obtained from practicing the method of the invention. The first is the finished version of the lattices generated during the diffusion phase. FIGS. 11A and 11C show this view of the labeled dataset from the array of FIG. 1. FIG. 11A is generated using conservative values of the tuning parameters 8 while FIG. 11C uses liberal values. FIGS. 11B and 11D show labeled close-ups of the bottom left corner corresponding to FIG. 3 of the array of FIG. 1. For legibility, only the labels suspicious (susp), ambiguous (ambg) and unlabeled (unlb) are included in the figures. Using conservative values for the parameters tend to label fewer points and result in one unlabeled centroid, while using liberal values tend to overlabel and result in six ambiguously labeled points.

The lattice visualization shows each edge (the line segment connecting two adjacent points in a row or column) as represented in six different local lattices. These lattices are well aligned if the six line segments appear as a single line segment. Small misalignments cause the line segment to appear thicker, and large misalignments produce shadows or completely separate traces. As a result, this way of displaying the data can explain any difficulties encountered by the algorithm. The "ambiguous" labels are due to the very slanted local lattice clearly visible in the liberal labeling program. This lattice does not show up in the conservative labeling program since its center is labeled suspicious and, therefore, is not used to label nearby points according to its local lattice.

Figure 12A:
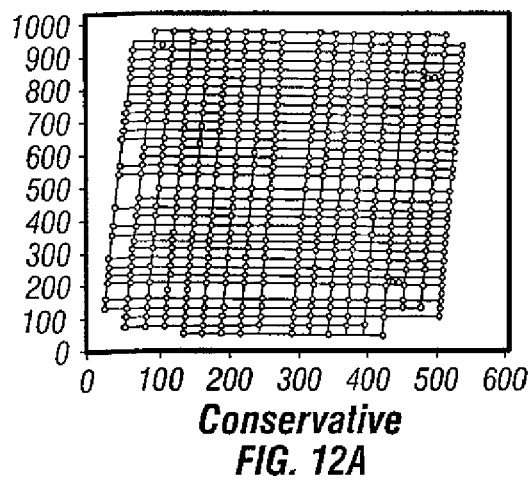
FIGS. 12A-12D are schematic drawings of a second visualization of the results from the practice of one embodiment of the method of the invention for the array shown in FIG. 1.
Figure 12B:
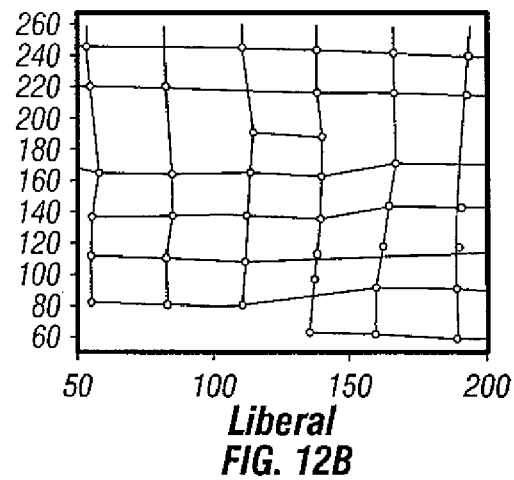
Figure 12C:
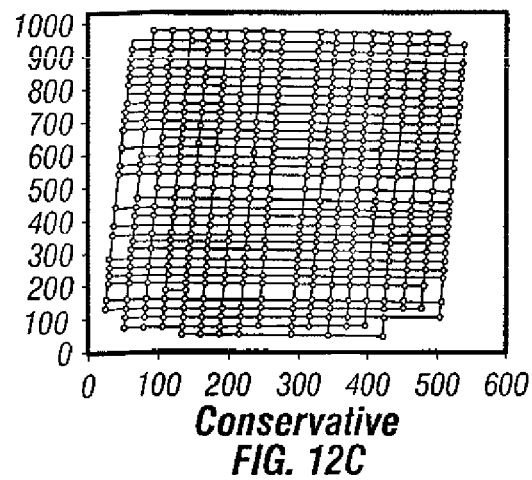
Figure 12D:
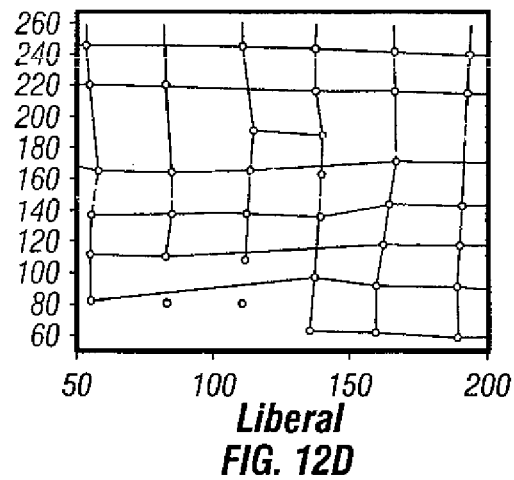
Figure 13A:
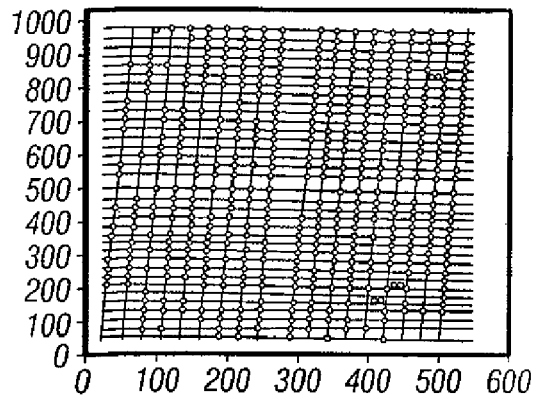
FIGS. 13A-13D are schematic drawings of a third visualization of the results from the practice of one embodiment of the method of the invention for the array shown in FIG. 1.
Figure 13B:
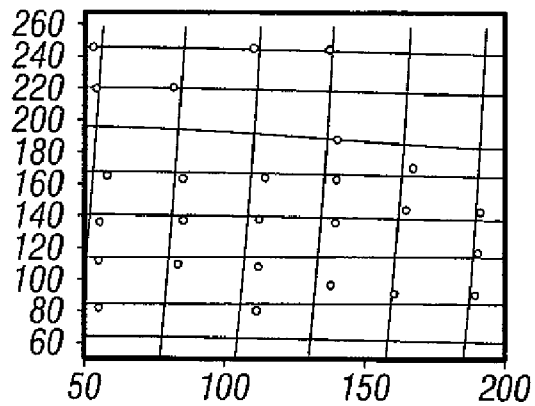
Figure 13C:
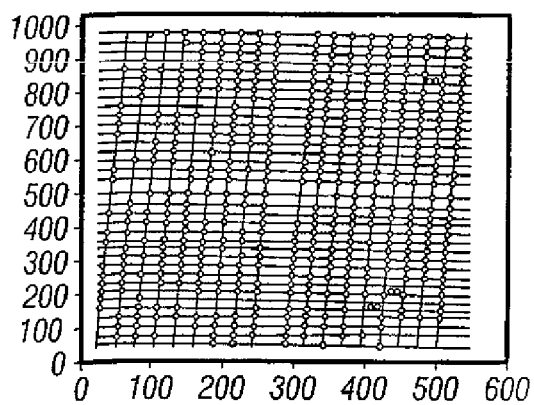
Figure 13D:
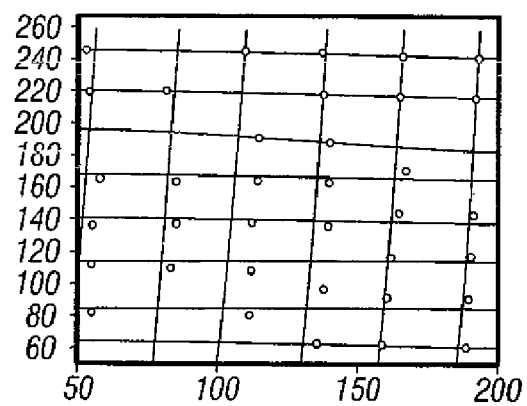
Figure 14A:
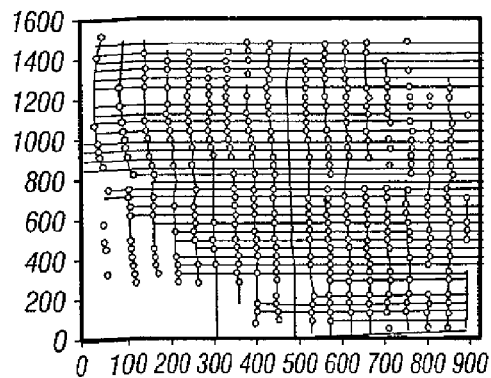
FIGS. 14A-14F are schematic drawings of one visualization of the results from the practice of one embodiment of the method of the invention for the array shown in FIG. 4.
Figure 14B:
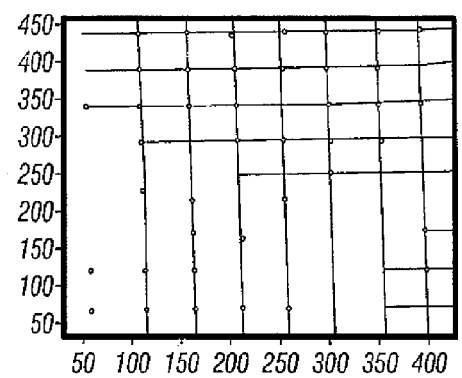
Figure 14C:
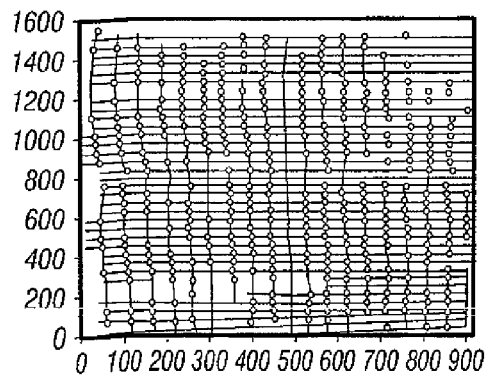
Figure 14D:
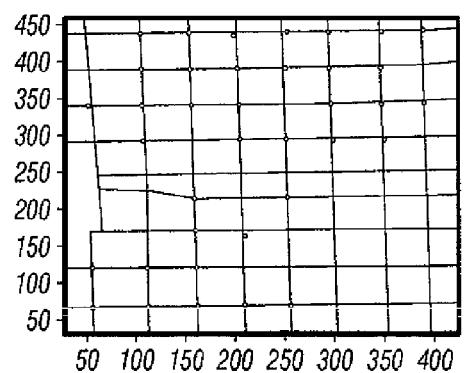
Figure 14E:
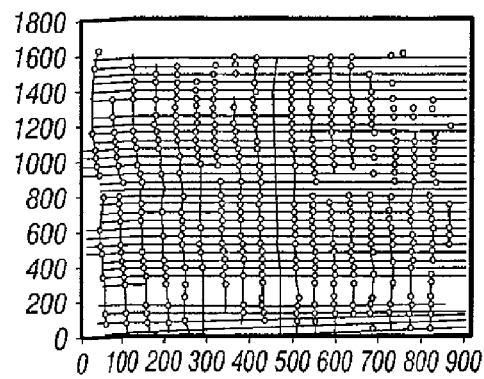
Figure 14F:
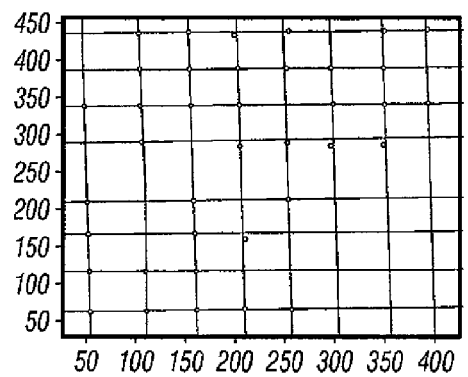
Figure 15A:
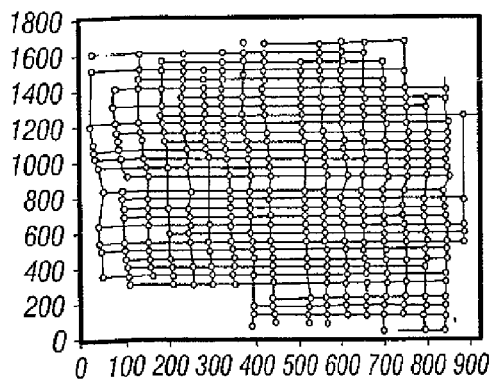
FIGS. 15A-15F are schematic drawings of a second visualization of the results from the practice of on embodiment of the method of the invention for the array shown in FIG. 4.
Figure 15B:
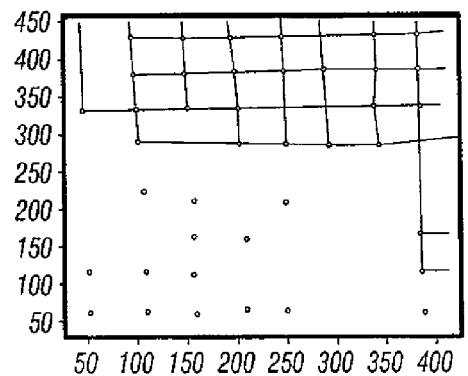
Figure 15C:
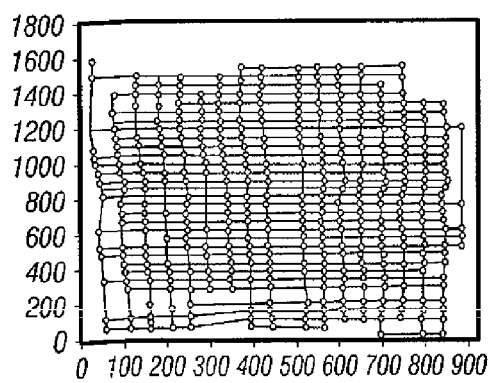
Figure 15D:
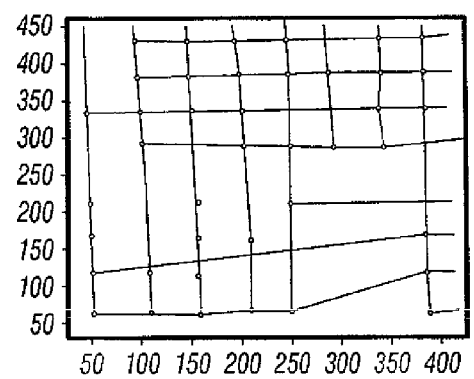
Figure 15E:
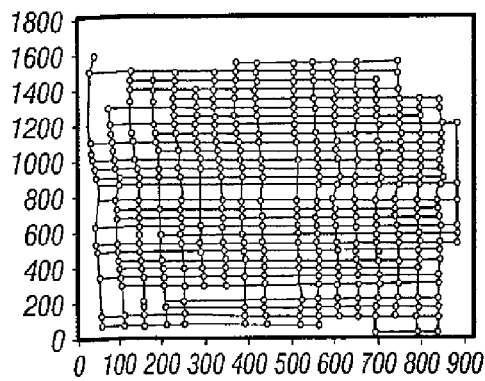
Figure 15F:
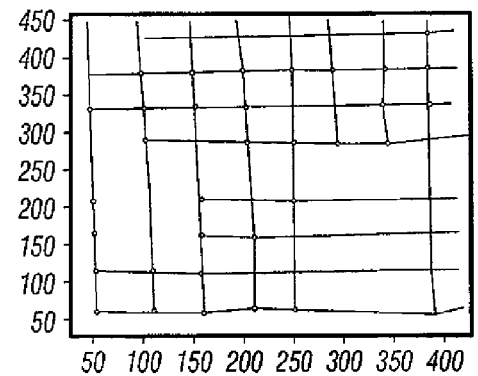
Figure 16A:
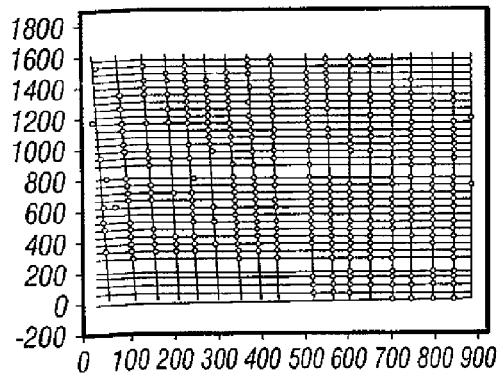
FIGS. 16A-16F are schematic drawings of a third visualization of the results from the practice of one embodiment of the method of the invention for the array shown in FIG. 4.
Figure 16B:
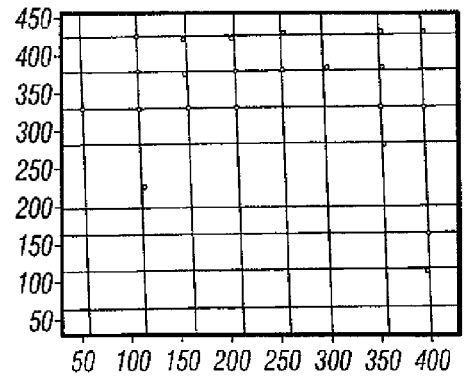
Figure 16C:
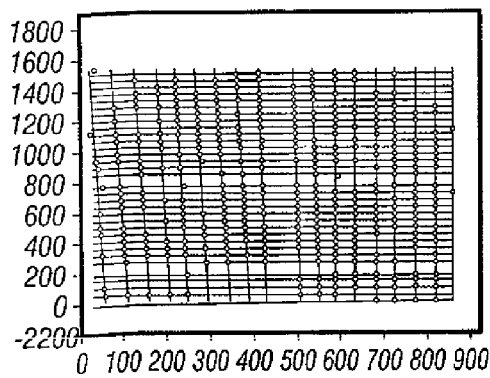
Figure 16D:
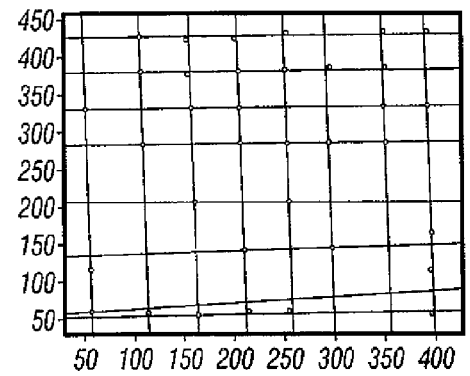
Figure 16E:
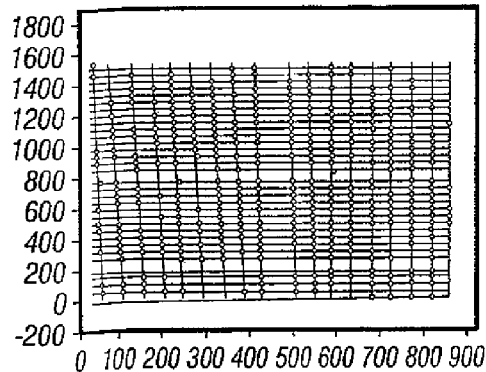
Figure 16F:
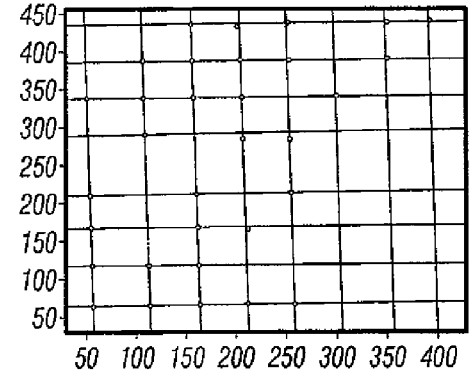

The second visualization of the results obtained from practicing the method of the invention is shown in FIGS. 12A-12D. FIGS. 12A and 12C show the results of the conservative and the liberal labeling for the dataset of FIG. 1. This view shows the grid generated by connecting each centroid to the adjacent centroids in its assigned row and column. This visualization displays the global structure resulting from the assignment of coordinates to centroids. The rows and columns can be easily discerned and deviations from a regular grid shape stand out. Irregularities in the grid pattern identify centroids with questionable assignments. For example, FIG. 12B shows the centroid left unlabeled when using conservative parameter values. The centroid is seen to lie at a "fault line." When using liberal values, FIG. 12D shows a shift by about half a grid spacing for the grid to the left relative to the grid line on the right. In this situation, it is better for the method to focus the attention of the user to this region than to come up with purported labels. Both extremes of parameter values fulfill this goal of pointing out problem areas.

The third visualization for this same dataset is shown in FIGS. 13A-13D. This graphical representation displays the lines that are the least squares fit to the centroids in each row and in each column. These lines summarize the global structure that has been assembled by the methods of the invention. Any nonlinear trends or deviations within a row or column are clearly visible within this representation and show the variation of local structures relative to the global structure. The lone pair of centroids in the $6^{th}$ row from the bottom arc very easy to spot in this view. In retrospect, it is also easy to spot these two points in the grid representation of FIGS. 12A-12D and represent another reason to call in a human operator. The "fault line" of FIGS. 12A-12D is also evident here in FIGS. 13A-13D.

The least squares lines in this representation can be used to extend the global structure into sparse regions and enable the assignment of row and column indices to centroids that were left unlabeled by the local structure method. The grid can also be extended across empty regions to connect isolated groups of centroids.

The closeness of a centroid to the nearest grid intersection can be used as a fourth measure of the confidence in its row and column assignment. The row and column assignments of centroids that are further from an intersection of the grid may be questionable. Using this measure would enable the method to perform further consistency checks thereby resolving some ambiguities and identifying others.

All three visual representations make it easy to spot the missing rows and columns. The grid and the lattice representations make clearly visible any misalignment between two intentionally separated regions. FIGS. 11A-11D show how a region boundary projects the local structure of its region into the missing row or column. A misalignment between the regions will appear as a series of misalignments between the local lattices centered on opposite sides of the missing row or column. Thus, the local structure for the boundary centroids spans the missing row or column and resolves the offset between the regions.

The sensitivity to parameter values is further illustrated by considering the labeling for the dataset from FIG. 4 shown in FIGS. 14A-14F (local lattice view), FIGS. 15A-15F (grid view) and FIGS. 16A-16F (lines view). Both the conservative and the liberal values for the parameters focus the operator attention on the problem area in the bottom left corner. Conservative parameter settings leave many points unlabeled, while liberal parameter settings label many points ambiguous. The best results are obtained by taking a conservative approach to allowing centers by keeping the conservative setting $\delta_1=0.15$, while allowing liberal labeling of neighbors from approved centers $\delta_3=0.25$. The third labeling in FIGS. 14A-14F, FIGS. 15A-15F and FIGS. 16A-16F show the results of the mixed setting $\delta_1=0.15$, $\delta_2=0.30$, and $\delta_3=0.25$. This labeling shows that the culprit is the point in the second column which lies a little too far above the fourth row from the bottom.

What is claimed is:

1. A system for analyzing an image representing a medical slide that includes a plurality of tissue samples arranged in an array, the system comprising a computer programmed to perform an algorithm comprising:
   forming a first measure that represents lattice parameters for only a portion of tissue samples within the image forming a first local lattice, and a second measure of how well the actual tissue samples fit to the first local lattice; and
   using said first and second measures to automatically locate and assign coordinates to samples in the array.

2. The system of claim 1, further comprising a camera for acquiring the image of the slide.

3. The system of claim 1, further comprising an xy stage for moving the slide to locations corresponding to images of the slide.

4. The system of claim 1, further comprising a barcode label reader for reading a barcode from the slide.

5. The system of claim 1, wherein the first local lattice structure is a 3×3 grid of points, the points comprising a centroid and eight nearest neighbors.

6. The system of claim 1, wherein the first local lattice structure is a 5×5 grid of points.

7. The system of claim 1, wherein the second measure represents a quality of fitness value, the quality of fitness value based on a least-mean-squares fit between a model lattice and an actual lattice.

8. The system of claim 1, wherein the algorithm includes finding a best first local lattice structure, and using the first and second measures when analyzing other areas of the medical slide to find a second local lattice structure therein.

9. A system for acquiring and analyzing an image representing a medical slide that includes a plurality of tissue samples arranged in an array, the system comprising:
means for acquiring the image; and
means for performing an image analysis algorithm on the acquired image, the algorithm comprising:
forming a first measure that represents lattice parameters for only a portion of tissue samples within the image forming a first local lattice, and a second measure of how well the actual tissue samples fit to the first local lattice; and
using said first and second measures to automatically locate and assign coordinates to samples in the array.

10. The system of claim 9, wherein the means for acquiring the image comprises a CCD camera.

11. The system of claim 9, further comprising means for associating identifying information from the slide with the acquired image.

12. The system of claim 11, wherein the means for associating identifying information from the slide with the acquired image comprises a barcode label reader.

13. The system of claim 9, wherein the second measure represents a quality of fitness value, the quality of fitness value based on a least-mean-squares fit between a model lattice and an actual lattice.

14. A system for acquiring and analyzing an image representing a slide that includes a plurality of tissue samples arranged in an array, the system comprising:
a microscope;
a camera operably coupled with the microscope and arranged to capture images of the slide; and
a computer programmed to perform an algorithm comprising:
forming a first local lattice representing a portion of the array of tissue samples;
determining a measure of how well the actual tissue samples within the array fit to the first local lattice; and
using the first local lattice and the measure to produce information indicative of actual locations of the tissue samples.

15. The system of claim 14, wherein the first local lattice includes lattice vectors representing a first local lattice structure of a specified size surrounding a center point, and the measure represents how well actual points of the tissue samples fit to the local lattice structure.

16. The system of claim 15, wherein the measure represents a quality of fitness value based on a least-mean-squares fit between actual points of the tissue samples and the first local lattice structure.

17. The system of claim 14, wherein the information comprises coordinating of tissue samples in the array.

18. The system of claim 14, wherein the algorithm further comprises finding a best local lattice structure and finding best lattice vectors that describe the local lattice structure.

19. The system of claim 14, wherein the algorithm further comprises finding possible locations which may falsely represent tissue samples and marking the locations as suspicious points.

20. The system of claim 14, wherein the algorithm further comprises finding actual points of the tissue samples which have a measure lower than a specified amount and marking the points as being suspicious points.

* * * * *

UNITED STATES PATENT AND TRADEMARK OFFICE
CERTIFICATE OF CORRECTION

PATENT NO. : 7,801,390 B2
APPLICATION NO. : 12/277147
DATED : September 21, 2010
INVENTOR(S) : Jose De La Torre-Bueno et al.

It is certified that error appears in the above-identified patent and that said Letters Patent is hereby corrected as shown below:

Column 2, line 32

Delete    "$n_{cols}*X/X_{max}$     (1)"

And insert therefore    --(1)    $n_{cols}*X/X_{max}$ --

Signed and Sealed this
Twenty-second Day of February, 2011

David J. Kappos
*Director of the United States Patent and Trademark Office*